United States Patent
Ogram

[19]

[11] Patent Number: 6,029,863
[45] Date of Patent: Feb. 29, 2000

[54] RESCUE DEVICE FOR BEE ATTACKS

[76] Inventor: Karen Ogram, 780 S. Freeman, Tucson, Ariz. 85748

[21] Appl. No.: 09/166,768

[22] Filed: Oct. 5, 1998

[51] Int. Cl.$^7$ ............................. B65D 83/14; A01N 25/00
[52] U.S. Cl. ................................. 222/402.15; 222/402.1; 424/405
[58] Field of Search ..................................... 222/175, 394, 222/402.1, 402.11, 402.15, 401; 239/337, 343

[56] References Cited

U.S. PATENT DOCUMENTS

| | | | |
|---|---|---|---|
| 2,281,142 | 4/1942 | Davis | 222/175 |
| 4,805,700 | 2/1989 | Hoover | 239/343 |
| 5,174,343 | 12/1992 | Rood | 222/394 |
| 5,480,658 | 1/1996 | Melman | 424/659 |
| 5,489,433 | 2/1996 | Aboud | 424/405 |

*Primary Examiner*—Kevin Shaver
*Assistant Examiner*—Eric Keasel
*Attorney, Agent, or Firm*—Mark E. Ogram P.C.

[57] ABSTRACT

A rescue apparatus to be used in the event of a bee attack in which a handheld cannister sprays a soapy or foamy mixture against the animal being attacked by the bees. The foam is ejected at least three feet to protect the rescuer from the bees. Also, the foam contains a local anaesthetic such as lidocaine hydrochloride and an insecticide. The local anaesthetic is used to both keep the foam from stinging the victim's eyes and also to deaden the site of the bee attack. The insecticide kills the bees to keep them from further attacks. The preferred insecticide is not harmful to humans.

13 Claims, 2 Drawing Sheets

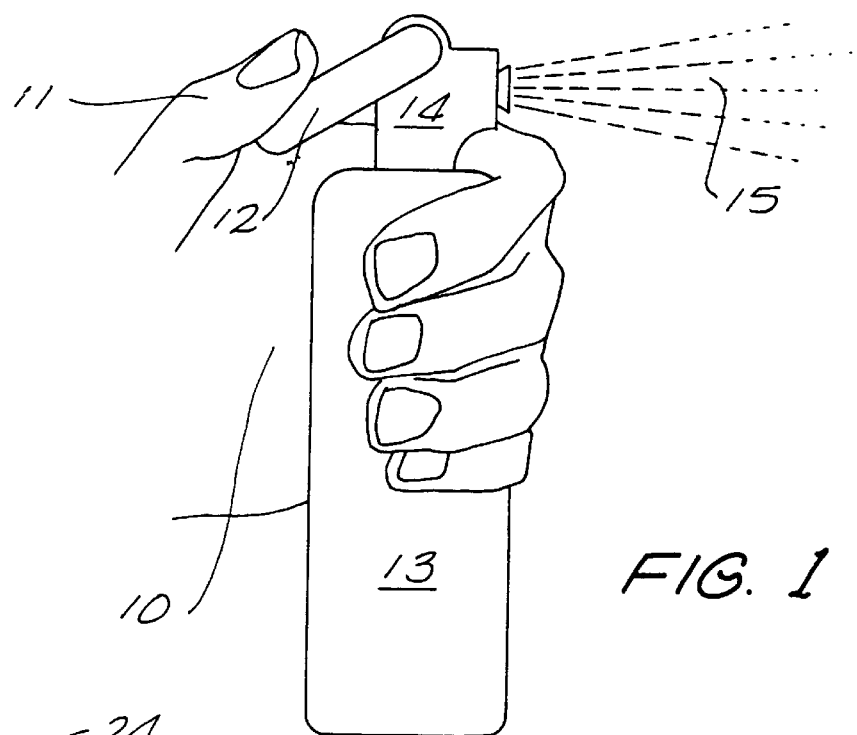
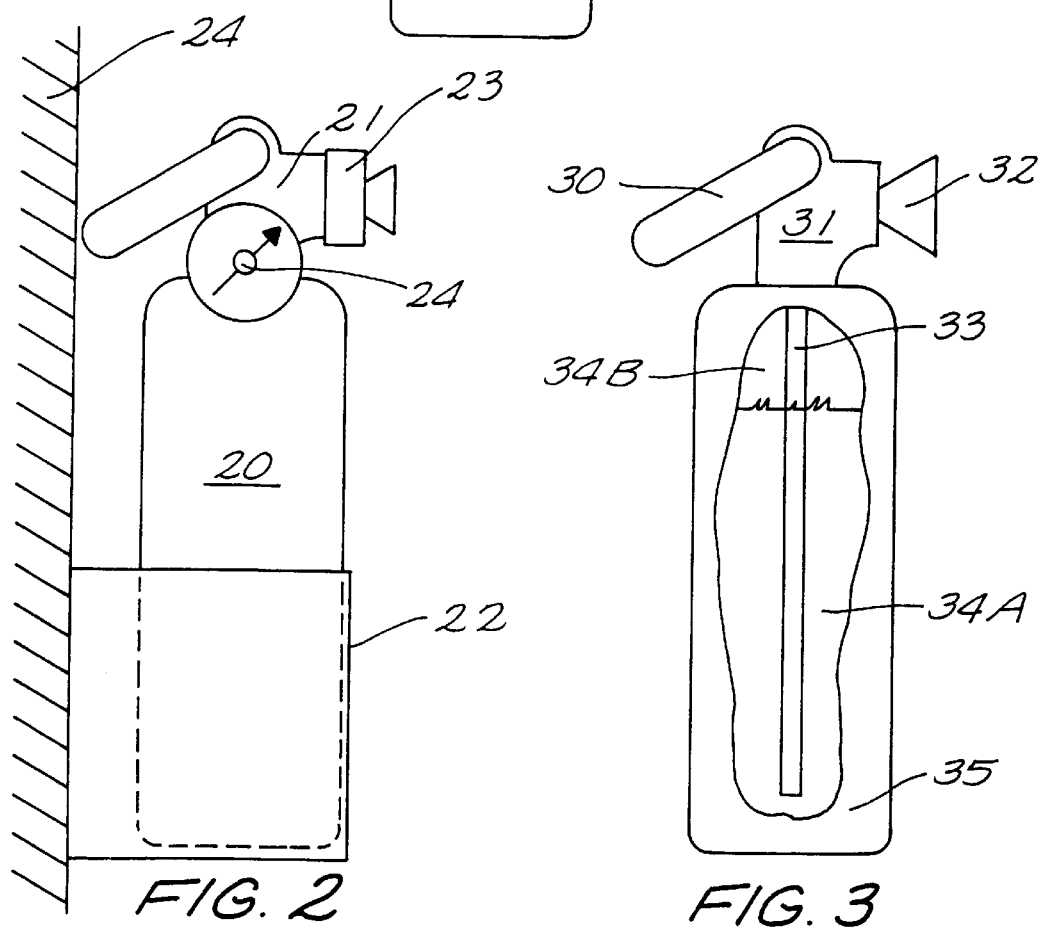

RESCUE DEVICE FOR BEE ATTACKS

BACKGROUND OF THE INVENTION

This invention relates generally to safety apparatus and more particularly to rescue apparatus for bee attacks.

While bees have proven to be of extreme importance within the agricultural industry, they have not always been viewed as "friendly". Even the relatively benign "European" bee is known to swarm and to attack without any obvious provocation.

This danger of bee attacks has only escalated as "Africanized" bees have migrated into the United States and have interacted with the "European" bees. The "Africanized" bees, while no more venomous than the "European" are known to attack with less provocation and to attack in heretofore unforeseen numbers. The assault by the "Africanized" bees is so intense and devoted, that its victims are often simply overwhelmed.

These attacks have become more common and include not only adults and children, but animals such as dogs and horses as well. In one attack on a horse, the animal was stung more than a thousand times before it died.

The attacks from the "Africanized" bees is so intense that any rescuer is put at a significant disadvantage. The rescuer, should they get too close to the victim, is likely to become a victim as well.

To combat bee attacks, fire departments have a soapy foam which they spray onto the hive. The soapy foam embeds the bees so that they are unable to fly or swarm. This removes the bees' threat.

Unfortunately, in almost all cases, by the time the fire department is able to respond to a bee attack, the victim is either extremely incapacitated or dead. The delay that it takes the fire department is more than sufficient for the bee attack to obtain its result.

It is clear from the foregoing that there is a need for an improved rescue apparatus suited for bee attacks.

SUMMARY OF THE INVENTION

The present invention creates a rescue apparatus which is to be used in the event of a bee attack. A handheld cannister sprays a soapy or foamy mixture against the animal being attacked by the bees.

The preferred embodiment is a handheld cannister which is easily grasped. A diameter of one inch is desired although larger sizes up to fire extinguisher sizes are also contemplated. The size of the cannister permits the cannister to be either carried on the body (similar to a mace cannister) or attached to a handy location (i.e. within the barn) like a fire extinguisher.

In the later case, to prevent confusion with a fire extinguisher, the cannister of this invention is colored differently than a fire extinguisher which is usually red. The color green is the preferred color.

The cannister contains the medium used to rescue the victim from the bee attach and is also pressurized so that the medium is propelled away from the user. Ideally, the foam is ejected at least three feet to protect the rescuer from the bees.

A variety of techniques are available to accomplish this ejection. These techniques are well known to those of ordinary skill in the art. One such technique provides for a pressurization of the cannister during its manufacture. When the valve on the cannister is opened, the medium is forced through the valve through a mixer to create the desired foam.

The foam used in this context is one of many and includes those traditionally used by rescue departments such as fire departments, and a "watery" soap mix. The soapy mixture impedes the bees' movement and flight capabilities; thereby eliminating further swarming or pursuit of the victim.

In one embodiment, the foam contains a local anaesthetic such as lidocaine hydrochloride. The local anaesthetic is useful in two ways: (1) it prevents the "stinging" of the eyes of the victim so that the victim does not become confused or distracted by the rescue operation; and, (2) the local anaesthetic also helps to reduce the pain caused by the bee stings, thereby "calming" the victim.

While lidocaine hydrochloride is the preferred local anaesthetic, those of ordinary skill in the art readily recognize a variety of other local anaesthetics which can be used in this context.

In yet another embodiment of the invention, an insecticide is also mixed into the foam. The insecticide should be chosen from those which do not injure the victim (usually a mammal). One such insecticide is described in U.S. Pat. No. 5,489,433, issued Feb. 6, 1996, to Aboud, incorporated hereinto by reference.

The insecticide is useful to further stop the assault by the bees as the swarming bees are killed. This also provides protection for the rescuer as the bees are then unable to turn their attention to the rescuer.

The invention, together with various embodiments thereof, will be more fully explained by the accompanying drawings and the following descriptions.

DRAWINGS IN BRIEF

FIG. 1 shows an embodiment of the invention being activated.

FIG. 2 illustrates a larger sized cannister secured to a wall or a post within a barn.

FIG. 3 is a cut-away view showing the pressurization of the preferred embodiment.

DRAWINGS IN DETAIL

Figure 4:
FIG. 4 illustrates the invention being used in a rescue situation.

FIG. 1 shows an embodiment of the invention being activated.

Operator 10 depresses lever 12 using thumb 11. This activates valve 14 which allows medium 15 to be ejected. Medium 15, in this embodiment contains water, detergent, an insecticide, and a local anaesthetic in the following percentage ranges by volume:

Water 70–90%

Detergent 4–10% insecticide 4–10% local anaesthetic 2–10%

Those of ordinary skill in the art readily recognize other formulas which will accomplish the tasks of this invention.

FIG. 2 illustrates a larger sized cannister secured to a wall or a post within a barn.

Bracket 22 is secured by screws or adhesive to wall 25. Bracket 22 is designed to accept cannister 20 therein and to permit easy removal of cannister 20.

In this embodiment, valve 21 is equipped with gauge 24 which provides a reading of the pressure within cannister 20. This assures that with a quick check of gauge 24, the operational status of the device is determined and if need be, cannister 20 is refilled or "recharged".

In this embodiment as well, valve 21 includes ariator 23 which injects air into the medium (not shown) as it is ejected from cannister 20. In this manner, a larger volume of foam is generated.

FIG. 3 is a cut-away view showing the pressurization of the preferred embodiment.

Cannister 35 is connected to valve 31. Activation of valve 31 is accomplished by depression of lever 30. Once activated, foam is ejected though nozzle 32.

Tube 33 communicates medium from the bottom of cannister 35 to valve 31. Within Cannister 35 is medium 34A and pressurized air 34B. The pressure and volume of the pressurized air 34B is chosen so that once valve 31 is activated, substantially the entirety of medium 34A is ejected through nozzle 32.

FIG. 4 illustrates the invention being used in a rescue situation.

Victim 40 is being attacked by swarm 41. In response, rescuer 10 activates cannister 13 which propels medium 15 against the swarm and onto victim 40. Because medium 15 is ejected at least three feet, rescuer 10 is never placed in harm's way and is able to readily assist victim 40.

It is clear that the present invention creates a highly improved and effective rescue apparatus to be used in the event of a bee attack.

What is claim is:

1. A stinging insect rescue apparatus comprising a handheld container containing a medium, said medium when ejected from said handheld container forming a soapy spray having a local anaesthetic therein propelled at least three feet.

2. The stinging insect rescue apparatus according to claim 1, further including an operator activated valve means for communicating said medium from said container against a target having bees thereon.

3. The stinging insect rescue apparatus according to claim 2, wherein said medium includes an insecticide adapted to kill bees.

4. A rescue apparatus for use in the event of a bee attack comprising:

a) a handheld container containing a medium including a local anaesthetic; and, b) means for ejecting said medium from said container such that when ejected, said medium forms a foam, c) wherein said means for ejecting propels said medium at least three feet from said handheld container.

5. The rescue apparatus according to claim 4, wherein said means for ejecting includes:

a) means for providing internal pressure to said container greater than ambient conditions; and, b) operator activated valve means for communicating said medium from said container against a target having bees thereon.

6. The rescue apparatus according to claim 4, wherein said local anaesthetic includes lidocaine hydrochloride.

7. The rescue apparatus according to claim 4, wherein said medium includes an insecticide adapted to kill bees.

8. The rescue apparatus according to claim 7, wherein said insecticide in not fatal to mammals.

9. The rescue apparatus according to claim 8, wherein said insecticide includes an hydroxy acyclic acid and a surfactant.

10. A rescue apparatus comprising:

a) a handheld container;

b) a medium contained within said handheld container, said medium adapted to create a soapy foam when ejected from said container, said medium including a local anaesthetic; and, c) operator activated means for ejecting said medium at least three feet from said container.

11. The rescue apparatus according to claim 10, wherein said local anaesthetic includes lidocaine hydrochloride.

12. The rescue apparatus according to claim 10, wherein said medium includes an insecticide adapted to kill bees.

13. The rescue apparatus according to claim 12, wherein said insecticide includes an hydroxy acyclic acid and a surfactant.

* * * * *